(12) United States Patent
Ho (10) Patent No.: US 7,762,260 B2
(45) Date of Patent: Jul. 27, 2010

(54) MASK MOUNTING MECHANISM

(75) Inventor: Peter Chi Fai Ho, Pittsburgh, PA (US)

(73) Assignee: Ric Investments, LLC, Wilmington, DE (US)

(*) Notice: Subject to any disclaimer, the term of this patent is extended or adjusted under 35 U.S.C. 154(b) by 1020 days.

(21) Appl. No.: 11/503,108

(22) Filed: Aug. 11, 2006

(65) Prior Publication Data

US 2007/0044797 A1   Mar. 1, 2007

Related U.S. Application Data (60) Provisional application No. 60/708,306, filed on Aug. 15, 2005.

(51) Int. Cl.
*A61M 11/00* (2006.01)
(52) U.S. Cl. .............. 128/207.11; 128/207.13
(58) Field of Classification Search ............ 128/200.24, 128/201.22, 204.18, 0.21, 0.29, 0.25, 205.25, 128/206.21, 0.24, 0.27, 0.28, 207.11, 0.13
See application file for complete search history.

(56) References Cited

U.S. PATENT DOCUMENTS

| | | | |
|---|---|---|---|
| 5,517,986 A | 5/1996 | Starr et al. | |
| 5,884,624 A | 3/1999 | Barnett et al. | |
| 6,397,847 B1 | 6/2002 | Scarberry et al. | |
| 6,467,483 B1 | 10/2002 | Kopacko et al. | |
| 6,470,886 B1 | 10/2002 | Jestrabek-Hart | |
| 6,516,802 B2 | 2/2003 | Hansen et al. | |
| 6,805,117 B1 | 10/2004 | Ho et al. | |
| 6,851,425 B2 | 2/2005 | Jaffre et al. | |
| 7,044,130 B2 * | 5/2006 | Jones et al. ............ | 128/206.21 |
| 7,066,179 B2 | 6/2006 | Eaton et al. | |
| 7,290,546 B2 * | 11/2007 | Sprinkle et al. ........ | 128/206.24 |
| 7,353,827 B2 * | 4/2008 | Geist ..................... | 128/206.21 |
| 7,568,483 B2 * | 8/2009 | Scarberry et al. ...... | 128/206.21 |
| 2004/0025883 A1 | 2/2004 | Eaton et al. | |
| 2004/0045551 A1 | 3/2004 | Eaton et al. | |
| 2005/0072428 A1 | 4/2005 | Ho et al. | |

FOREIGN PATENT DOCUMENTS

WO  WO 2004014454  * 2/2004

* cited by examiner

*Primary Examiner*—Steven O Douglas
(74) *Attorney, Agent, or Firm*—Michael W. Haas (57) ABSTRACT

A mask mounting mechanism for use in connection with a patient interface device including an extension member with a first end and a second end, wherein the first end is attached to a portion of the mask, and the second end extends from and is spacially separated from the mask. The mask mounting mechanism further includes an attachment mechanism on the second end of the extension member for engaging a strap of the mask attachment assembly. The second end of the extension member minimizes the potential for the attachment mechanism and the strap from contacting a user's face.

20 Claims, 6 Drawing Sheets

MASK MOUNTING MECHANISM

CROSS-REFERENCE TO RELATED APPLICATIONS

This application claims priority under 35 U.S.C. §119(e) from provisional U.S. Patent Application No. 60/708,306 filed Aug. 15, 2005 the contents of which are incorporated herein by reference.

BACKGROUND OF THE INVENTION

1. Field of the Invention

The present invention generally relates to structures and assemblies for use in connection with a patient interface device, such as a respiratory mask, and a mask attachment assembly, such as headgear having straps to retain the mask in a sealed position on a user's face. In particular, the present invention is related to a mask mounting mechanism connected to the respiratory mask that prevents a portion of the attachment assembly and/or the straps from contacting the user's face, which provides additional convenience, ease-of-use, ease-of-adjustment, and improved comfort to the patient.

2. Description of the Related Art

It is well known to treat a medical disorder or to diagnose, treat, or monitor the condition of the patient using medical equipment. For example, a patient may be monitored and treated for various sleep disorders in a lab or in some other setting. An example of a type of sleep disorder is sleep apnea. Obstructive sleep apnea is characterized by the collapse of the upper airway during sleep, while central sleep apnea is characterized by the suspension of all respiratory movement. Obstructive sleep apnea and central sleep apnea may be combined in a condition referred to as mixed apnea.

In order to diagnose and/or treat such medical disorders, various equipment and devices are utilized. Further, there are numerous situations where it is necessary or desirable to deliver a flow of breathing gas, non-invasively, to the airway of a patient, i.e., without intubating the patient or surgically inserting a tracheotomy tube in their trachea. For example, it is known to ventilate a patient using a technique known as non-invasive ventilation. It is also known to deliver continuous positive airway pressure (CPAP) or variable airway pressure, which varies with the patient's respiratory cycle or a monitored condition of the patient, to treat a medical disorder, such as sleep apnea syndrome, in particular, obstructive sleep apnea (OSA), congestive heart failure, stroke, Cheynes-Stokes respiration, etc. Non-invasive ventilation and pressure support therapies involve the placement of a patient interface device, which is typically a nasal or nasal/oral mask, on the face of a patient to interface the ventilator or pressure support device with the airway of the patient, so that a flow of breathing gas can be delivered from the pressure/flow generating device to the airway of the patient.

A CPAP device delivers a flow of fluid to the airway of the patient throughout the patient's breathing cycle in order to "splint" the airway open, thereby preventing its collapse during sleep. In another type of treatment, bi-level positive pressure therapy is provided to the patient, in which the pressure of air delivered to the patient's airway varies or is synchronized with the patient's breathing cycle to maximize therapeutic effect and comfort to the patient. A pressure support device may also provide "bi-level" pressure support, in which a lower pressure is delivered to that patient during the patient's expiratory phase then during the inspiratory phase.

It is also known to provide an auto-titration positive pressure therapy in which the pressure provided to the patient changes based upon the detected conditions of the patient, such as whether the patient is snoring or experiencing an apnea, hypopnea, or upper airway resistance. Such a device adjusts the pressure delivered to the patient, based on whether or not the patient is snoring. For example, a pressure support device may actively test the patient's airway to determine whether obstruction, complete or partial, could occur and adjust the pressure output to avoid this result.

Other modes of providing positive pressure support to a patient are known. For example, a proportional assist ventilation mode of pressure support provides a positive pressure therapy in which the pressure of gas delivered to the patient varies with the patient's breathing effort to increase the comfort to the patient. Proportional positive airway pressure (PPAP) devices deliver breathing gas to the patient based on the flow generated by the patient.

For purposes of the present invention, the phrase "pressure support system", "pressure support device", or "positive pressure support" includes any medical device or method that delivers a flow of breathing gas to the airway of a patient, including a ventilator, CPAP, bi-level, PAV, PPAP, or auto-titration pressure support system.

Typically, gas such as oxygen or air is delivered by a pressure generating device, which may be, in turn, in fluid communication with an oxygen tank. The oxygen flows from the source through the regulator devices, through the pressure generating device and further through a conduit into a patient interface. The pressure generating device and the conduit, such as a gas hose, are considered the patient circuit. A coupling assembly is required for connecting the patient circuit to the patient interface device.

In a conventional pressure support system, a flexible conduit is coupled to an exit conduit from the pressure generating device. The flexible conduit forms part of the patient circuit that carries the flow of breathing gas from the pressure generating system to the patient interface device. In a support system, the patient interface device connects the patient circuit with the airway of the patient so that the elevated pressure gas flow is delivered to the patient's airway.

In order to provide gas or, as discussed above, oxygen, to a patient, the patient must use a patient interface device, such as a nasal mask (including external cushions and/or internal prongs), nasal/oral mask, full-face mask, nasal cannula, oral mouthpiece, tracheal tube, endotracheal tube, or hood. Typically patient interface devices include a shell having a cushion attached to the shell that contacts the surface of the patient. The shell and cushion are held in place by a headgear that wraps around the head of the patient. Together, the mask and headgear form the patient interface assembly. A typical mask attachment assembly includes headgear having flexible, adjustable straps that extend from the mask to attach the mask to the patient. Other techniques for attaching a patient interface device use a vice-like device that anchors at the front and back of the patient's head to support the mask on the user. See, e.g., U.S. Pat. No. 6,516,802.

Because such patient interface devices are typically worn for an extended period of time, a variety of concerns must be taken into consideration. For example, in providing CPAP or other positive pressure therapy to treat sleep disordered breathing, the patient normally wears the patient interface device all night long while he or she sleeps. In order to be successful in these applications, a patient interface needs to take into consideration two often competing goals: comfort and technical effectiveness. Failure to achieve either goal is likely to result in low efficacy. A comfortable, but technically ineffective, patient interface may achieve superior patient compliance; however, its technical ineffectiveness will minimize the therapeutic benefit achieved. Alternatively, a technically effective, but uncomfortable, patient interface may be capable of treating a patient; yet, the lack of comfort often results in low patient compliance. This also undermines the therapeutic benefit obtained by the patient. Thus, further advancements for interfacing a pressure support system to the airway of a patient are desired.

It is known to maintain such interface devices on the face of a patient by a headgear having upper and lower straps, each having opposite ends threaded through connecting elements provided on the opposite sides and top of the interface device, such as a mask. Because such masks are typically worn for an extended period of time, it is important that the headgear provides a sufficient seal against a patient's face without causing discomfort. One known headgear is disclosed in U.S. Pat. No. 5,517,986 to Starr et al. ("the '986 patent") which has been assigned to the Assignee of the present invention and is hereby incorporated by reference. This headgear includes a headpiece 12 adapted to fit the crown and back of a patient's head. Lower straps 30 and 32 provide a two-point connection with a gas delivery mask 40. See FIG. 1 of the '986 patent. Depending straps 18 and 20, extending from headpiece 12, are connected to, and moveable relative to, the lower straps. Additionally, a pair of upper straps 56 and 58 can be used to provide a four-point connection with the gas delivery mask if needed as seen in FIG. 7 of the '986 patent.

As discussed above, adjustability of the mask and/or the headgear, together with increased patient comfort, is paramount; however, maintenance of the seal between the mask and the user's face must be adequately achieved. According to the prior art, various headgear have been developed that position the straps in various locations with respect to the mask in order to effect this seal. For example, in U.S. Pat. No. 6,470,886 to Jestrabek-Hart ("the '886 patent"), a clip 23 (FIGS. 14-16) or extender 20, 22 (FIGS. 8-11) is used to displace the bottom strap (or lip strap) of headgear down from the mask. However, the clips 23 or extenders 20, 22 of the '886 patent merely move the point of strap contact to a different position, namely just below the patient's lower lip. Although this effectively moves the contact point, this position may be incapable of providing either comfort or an effective seal. Locating the strap in this location may impede the user from moving their jaw or cause abrasion to the user's skin thus causing discomfort. In addition as the user movers their jaw, the straps may be biased in a manner that may result in reducing the effectiveness of the seal. Accordingly, the prior art headgear and masks still evidence contact between the strap (or extender and strap) and the patient's face. This configuration may result in devices that are perceived by the user as being unsightly, uncomfortable, and inconvenient to use. In addition, it is difficult to maintain an adequate seal in these devices.

SUMMARY OF THE INVENTION

Accordingly, it is an object of the present invention to provide a mask mounting mechanism that addresses one or more of the above-identified concerns and overcomes the shortcomings of conventional mask mounting assemblies, masks, headgear, and the like in the gas delivery art. In accordance with the broad teachings of the present invention, a mask mounting system is provided.

In one aspect, the mask mounting mechanism of the present invention is for use in connection with a patient interface device having a mask and a mask attachment assembly having straps to retain the mask in a sealed position on a user's face. The mask mounting mechanism includes an extension member having a first end and a second end, and the first end of the extension member is directly or indirectly attached to a portion of the mask. The second end of the extension member extends from and is spatially separated from the mask. The mask mounting mechanism includes an attachment mechanism positioned on the second end of the extension member for engaging the straps of the mask attachment assembly. As such, the second end of the extension member minimizes the potential for the attachment mechanism and the strap engaged therewith from contacting the user's face.

In another aspect of the invention, a patient interface device, including a mask having a mask wall with a mask port extending therethrough, is provided. A mask conduit coupling is in fluid communication with the mask port, and a mask attachment assembly, having straps, retains the mask in a sealed position on a user's face. The device further includes a mask mounting mechanism, including: (i) an extension member having a first end and a second end, the first end of the extension member directly or indirectly attached to a portion of the mask; and the second end of the extension member extending from and spatially separated from the mask; and (ii) an attachment mechanism positioned on the second end of the extension member for engaging a strap of the mask attachment assembly. The second end of the extension member minimizes the potential for the attachment mechanism and at least a portion of the strap engaged therewith from contacting the user's face.

These and other features and characteristics of the present invention, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and the claims, the singular form of "a", "an", and "the" include plural referents unless the context clearly dictates otherwise.

DETAILED DESCRIPTION OF THE EXEMPLARY EMBODIMENTS

The present invention is directed to a mask mounting mechanism 10 as illustrated in various embodiments in FIGS. 1-8. In particular, and as illustrated in schematic form in FIGS. 1 and 2, mask mounting mechanism 10 is designed to be used in connection with a patient interface device 100, which includes a mask 102 and a mask attachment assembly 104. Mask 102 can be a nasal mask (including an external cushion and/or internal prongs), an oral mask, a nasal and oral mask, full face mask or other similar devices and structures as are known in the art. Mask attachment assembly 104 includes at least one, and typically multiple straps 106 for retaining mask 102 in a sealed position with respect to a user's face A. As is known in the art, mask attachment assembly 104 can be a three-point attachment assembly, a four-point attachment assembly.

Mask 102 includes a mask wall 108 having a mask port 110 extending therethrough. Such an arrangement is known in the art, and mask port 110 allows for further attachment to other assemblies in order to provide gas into mask 102 for inhalation by the patient. In particular, mask 102 serves to provide a user, or patient, with gas, such as oxygen, air, room air, etc., and this gas flows through mask port 110 into mask 102 for inhalation.

As seen in FIGS. 3-7, a mask conduit coupling 112 is connected to mask 102 and allows for a sealed transfer of gas through mask conduit coupling 112, further through mask port 110 and into mask 102. Mask conduit coupling 112 may also include an exhaust port 113 for permitting the exhausted breath of the patient to flow from mask 102, through mask port 110, further through mask conduit coupling 112 and out exhaust port 113 to the ambient atmosphere. One example of such an exhaust port 113 is shown and described in U.S. Pat. No. 6,851,425, which has been assigned to the Assignee of the present invention and incorporated herein by reference.

Figure 2:
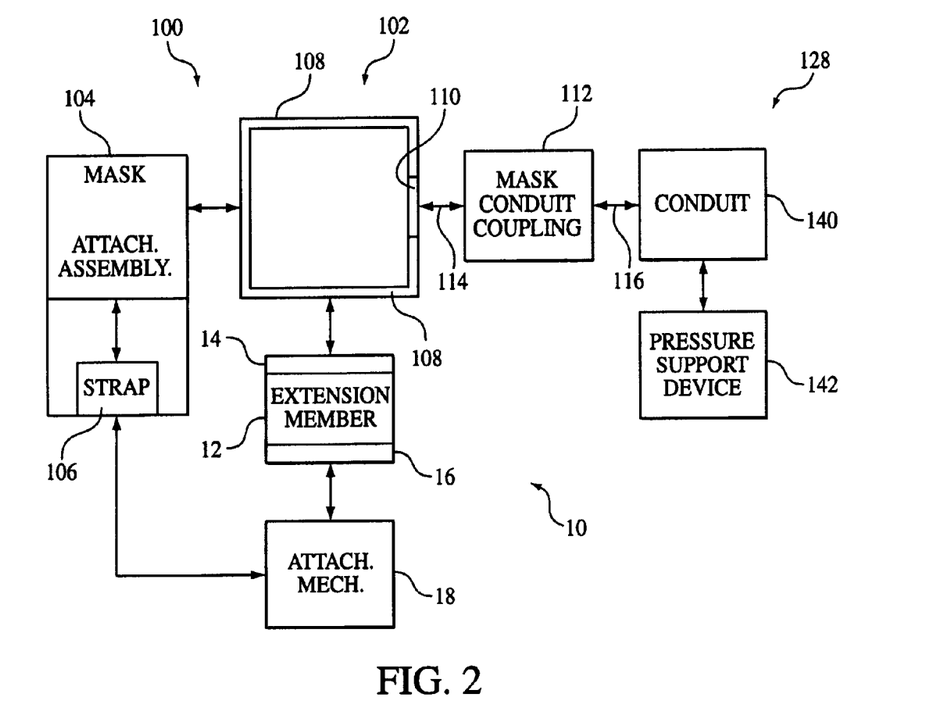
FIG. 2 is a schematic view of a patient interface device and a mask mounting mechanism according to the principles of the present invention for use in connection with a patient circuit.

The mask conduit coupling 112 has a first end 114 and a second end 116. First end 114 of mask conduit coupling 112 is attached to mask 102. As seen in FIG. 2, patient circuit 128 may include a conduit 140 and a pressure support device 142. Patient circuit 128 is also an arrangement that is known in the art. In particular, patient circuit 128 typically includes conduit 140 in fluid communication with a pressure support device 142. In operation, the gas, typically oxygen or air, flows from pressure support device 142, which may receive oxygen from an oxygen tank or other similar gas sources, through conduit 140, through mask conduit coupling 112 and mask port 110 and into mask 102, as discussed above. In this manner, the patient receives gas delivery for inhalation.

The mask attachment assembly includes straps 106 to retain mask 102 in a sealed position on the user's face A. Mask attachment assembly 104 may be in the form of a headgear wearable by the patient having straps 106 attached thereto. Further, patient interface device 100 of the present invention includes mask mounting mechanism 10, as discussed in detail hereinafter.

Straps 106 can be adjusted by the user or patient and, as discussed hereinafter, using a ball-and-socket arrangement or other attachment arrangement, straps 106 can be removed from mask mounting mechanism 10. In another embodiment, patient interface device 100 includes a forehead support assembly having a forehead contact member 124, which is attached to and extends from mask 102. An example of one type of forehead support assembly is shown and described in U.S. Publication No. 2004/0045551, which has been assigned to the Assignee of the present invention and incorporated herein by reference. At least a portion of forehead contact member 124 contacts a portion of a user's forehead B. As is known in the art, forehead contact member 124 may include a padded element 126 for comfortably contacting the user's forehead B. For example, padded element 126 can be a gel-filled cushion, such as a detachable gel-filled cushion, which is shown and described in U.S. Pat. Nos. 5,884,624 and 6,397,847, which have been assigned to the Assignee of the present invention and incorporated herein by reference.

Figure 1:
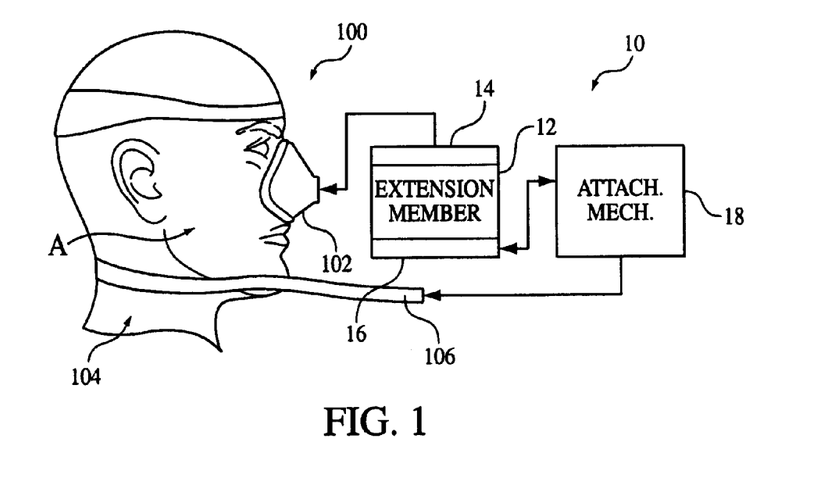
FIG. 1 is a schematic view of a mask mounting mechanism according to the principles of the present invention for use in connection with a patient interface device having a mask attachment assembly.
Figure 3:
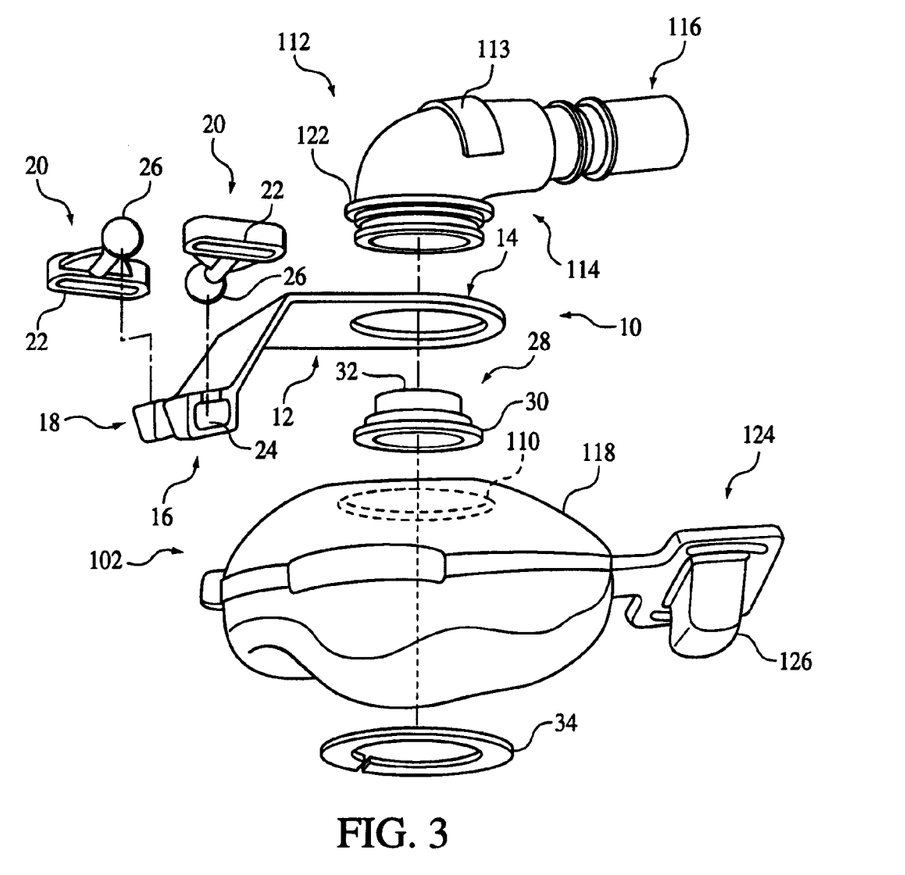
FIG. 3 is an exploded perspective view of a mask mounting mechanism according to the principles of the present invention for use with a patient interface device.

As seen in FIGS. 1-3, mask mounting mechanism 10 includes an extension member 12 having a first end 14 and a second end 16. First end 14 of extension member 12 is directly or indirectly attached to a portion of mask 102. Further, second end 16 of extension member 12 extends from mask 102 and is spacially separated from mask 102.

Mask mounting mechanism 10 also includes an attachment mechanism 18 positioned on or otherwise engaged with extension member 12, such as second end 16 of extension member 12. Attachment mechanism 18 engages with straps 106 of mask attachment assembly 104.

It is envisioned that mask mounting mechanism 10 can be used in connection with and retrofitted on a previously-existing mask 102. Alternatively, the patient can be supplied with an assembled patient interface device 100 according to the present invention. In either case, mask mounting mechanism 10 serves to minimize the potential for attachment mechanism 18 and straps 106 of mask attachment assembly 104 from contacting the user's face A.

In one embodiment, extension member 12 extends outwardly from the mask towards the user's chin and lip area a given distance. In this orientation, extension member 12 minimizes the potential for contact between the user's face A and mask mounting mechanism 10. Another unique aspect of extension member 12 is that by extending outwardly from the mask, extension member 12 creates an extended lever between mask 102 and straps 106. By extending outwardly, the torque, or moment, applied by extension member 12 is increased for a given applied force. One skilled in the art can best appreciate that the torque, or moment, applied may be adjusted by either increasing or decreasing the length of extension member 12 as desired.

It is known that the seal between mask 102 and the region between the user's nose and upper lip often becomes compromised. This tendency can be further exacerbated by have a mounting mechanism which contacts various features on the front of the user's face which may be moved by the user such as the checks, jaw, etc. As shown in FIG. 3, the seal is enhanced in this troublesome region by the unique location of extension member 12, which extends a distance away from this region. In contrast, masks which utilize straps that are connected inwardly inboard on the mask results in a smaller lever and thus requires the application of additional force to achieve an adequate seal.

One skilled in the art can best appreciate that extension member 12 may extend in a variety of different orientations in order to apply the moment in a desirable direction to enhance the seal created with the user's face A and maximize comfort. In other applications, a poor seal may occur in other regions about mask 102 due to the user's unique facial characteristics or the particular design of mask 102. The inventors of the present invention contemplate that extension member 12 may be directed in a variety of other directions in order to enhance the seal integrity regardless of the particular region in which the seal integrity has become compromised. For instance, in the event that the seal has become compromised at the interface between the user's cheeks and mask 102, extension members 12 could be directed laterally. In addition, a variety of different extension members 12 may be formed having differing lengths to adjust the applied moment. Of course, these extension members 12 may be formed integrally with mask 102 or separately from mask 102 and coupled thereto in a modular construction.

The present invention further contemplates that extension member 12 may be pivotally connected to mask 102, such that the direction extension member 12 extends from mask 102 is adjustable. This may be particularly advantageous since these masks 102 are commonly used by patients while they are sleeping. As is well known, a sleeping user may adjust the orientation of their head, which often results in modifying the forces exerted on mask 102. The pivotable coupling permits extension member 12 to be self-adjusting as the forces exerted on mask 102 change without requiring user manipulation.

Figure 4:
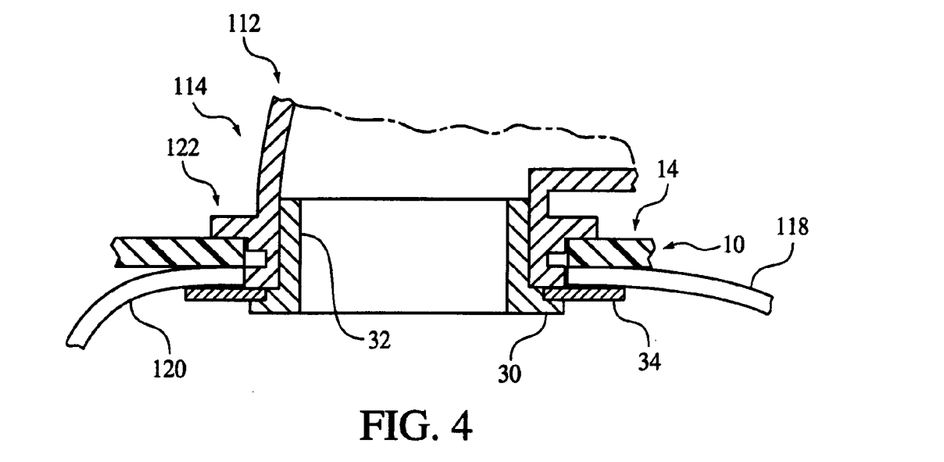
FIG. 4 is a partial side section view about a connection area of the mask mounting mechanism and patient interface device of FIG. 3.
Figure 5:
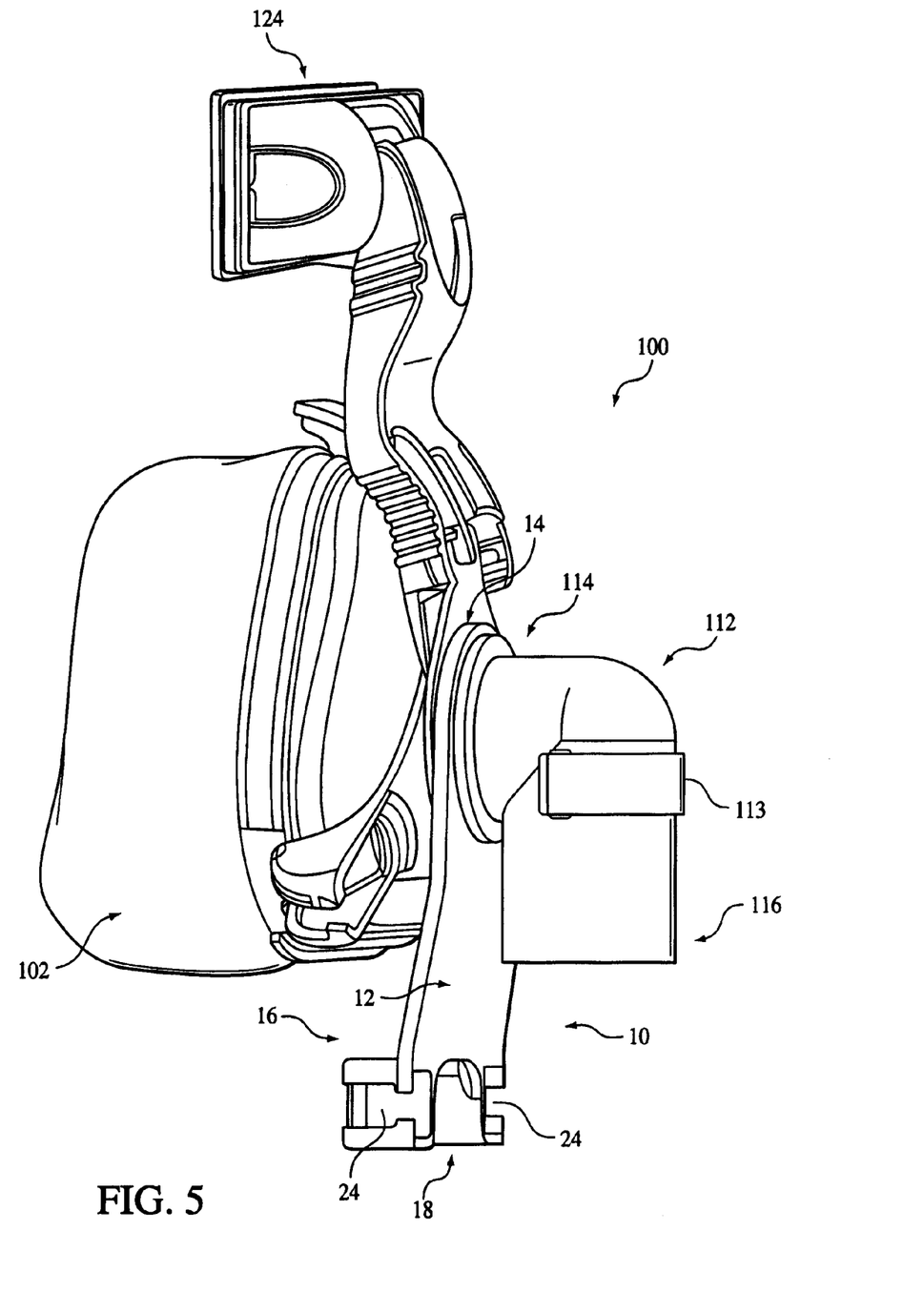
FIG. 5 is a perspective view of a mask mounting mechanism according to the principles of the present invention as attached to a patient interface device.
Figure 6:
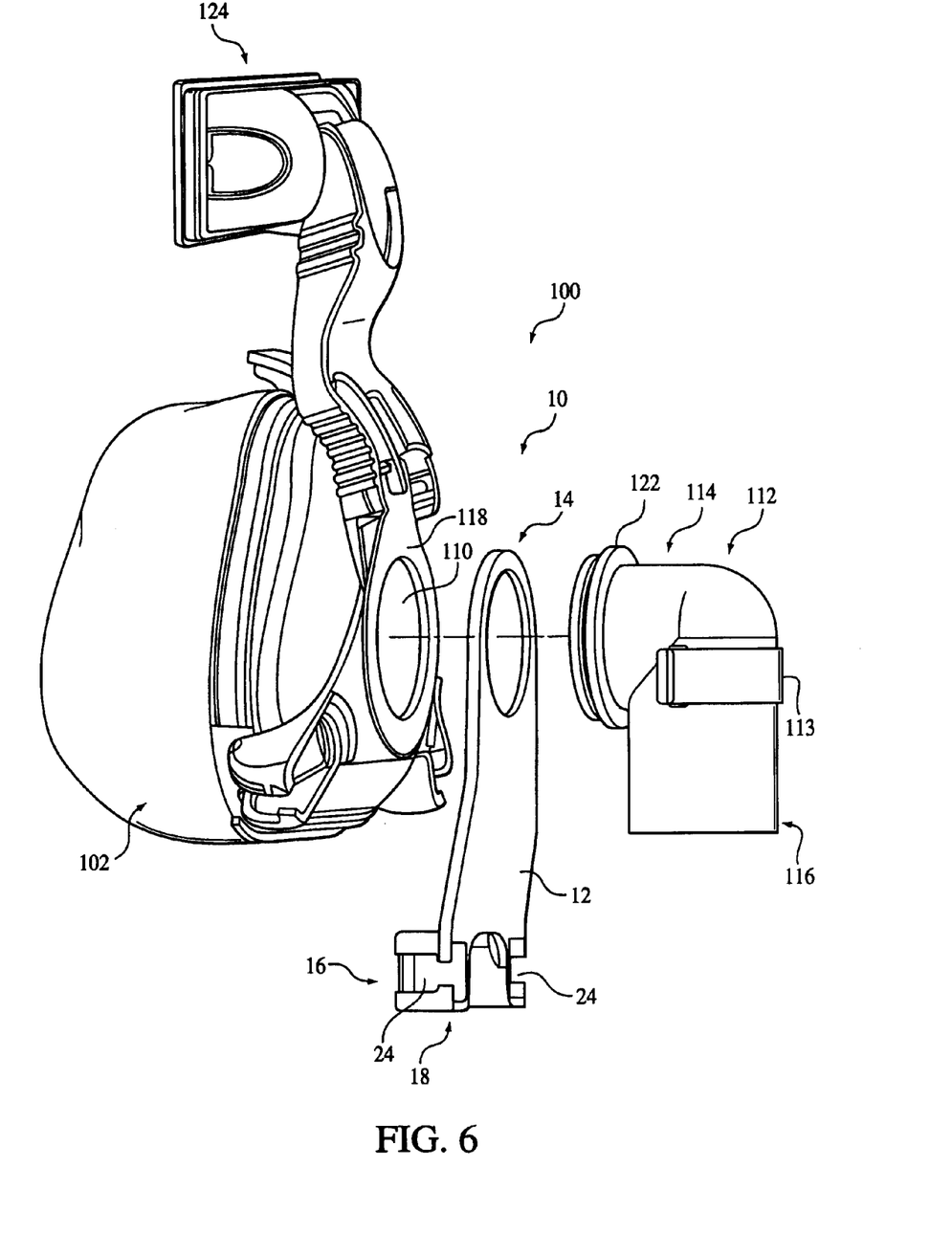
FIG. 6 is an exploded perspective view of the mask mounting mechanism and patient interface device of FIG. 5.

As best seen in FIGS. 3 and 4, in one embodiment of the present invention, first end 14 of extension member 12 is attached to mask 102 at some position that is substantially adjacent mask port 110. In this embodiment, mask mounting mechanism 10 also includes a mask conduit connector 28 for attaching first end 14 of extension member 12 between an outer surface 118 of mask 102 and first end 114 of mask conduit coupling 112.

In order to effect appropriate attachment of the various components, as well as provide an effective seal, mask conduit connector 28 includes a rim portion 30 and an extension portion 32. Rim portion 30 of mask conduit connector 28 abuts a washer element 34. Washer element 34, in turn, abuts an inner surface 120 of mask wall 108. Still further, extension portion 32 extends through mask port 110.

First end 114 of mask conduit coupling 112 is engaged with extension portion 32 of mask conduit connector 28. In this manner, mask mounting mechanism 10 and, in particular, first end 14 of extension member 12, is engaged between outer surface 118 of mask 102 and first end 114 of mask conduit coupling 112, with washer element 34 providing an additional seal around mask port 110.

In another embodiment, first end 114 of mask conduit coupling 112 includes a rim portion 122. It is this rim portion 122 that abuts first end 14 of extension member 12 and urges first end 14 of extension member 12 against outer surface 118 of mask 102. This relative positioning and "sandwiched" relationship is illustrated in FIG. 4.

It is also envisioned that extension member 12 is rotatable with respect to mask 102. Accordingly, first end 14 of extension member 12 is held between outer surface 118 of mask 102 and mask conduit coupling 112, but it is capable of swiveling or rotating therebetween. This rotation allows for the passive adjustment of mask 102. This is beneficial as the movement of straps 106 will only move the extension member, without moving mask 102. Therefore, the seal between mask 102 and the user's face A will not be broken.

Extension member 12 may be manufactured from a variety of materials. For example, extension member 12 may be manufactured from a flexible material or a rigid material. In a preferred embodiment, extension member 12 is manufactured from a substantially rigid material, such that when straps 106 are tightened they do not pull attachment mechanism 18 and straps 106 against the user's face A.

Attachment mechanism 18 is positioned proximate second end 16 of extension member 12, and is used to engage one or more of the straps of mask attachment assembly 104. In one embodiment, attachment mechanism 18 is one or more clip elements 20 attachable to a portion of second end 16 of extension member 12. These clip elements 20 each include a buckle 22 or collar for engaging one or more straps 106 of mask attachment assembly 104. The straps can be fed through buckle 22 and secured in place by a hook and loop type adjustable fastener or sewn in place. Of course, a variety of other fasteners could be utilized to connect straps 106 to clips 20 such as buttons, rivets, snaps, adhesive and the like without departing from the scope of the present invention. Appropriate attachment of strap 106 to buckle 22 of clip element 20 is well known in the art, and illustrated in FIG. 7.

In addition, attachment mechanism 18 also includes a respective slot 24 on extension member 12, such that a portion of clip element 20 can be movingly engaged within slot 24. In this manner, clip element 20, as well as buckle 22 and attached strap 106, are movable and/or rotatable with respect to second end 16 of extension member 12. Such an arrangement provides much more flexibility of movement to the patient, but maintains the appropriate seal with respect to the user's face A. In combination with the self-adjusting features of the extension member described above, the self-adjustability of attachment mechanism 18 further enhances the seal integrity between mask 102 and the user's face A, as well as enhances user comfort.

Figure 7:
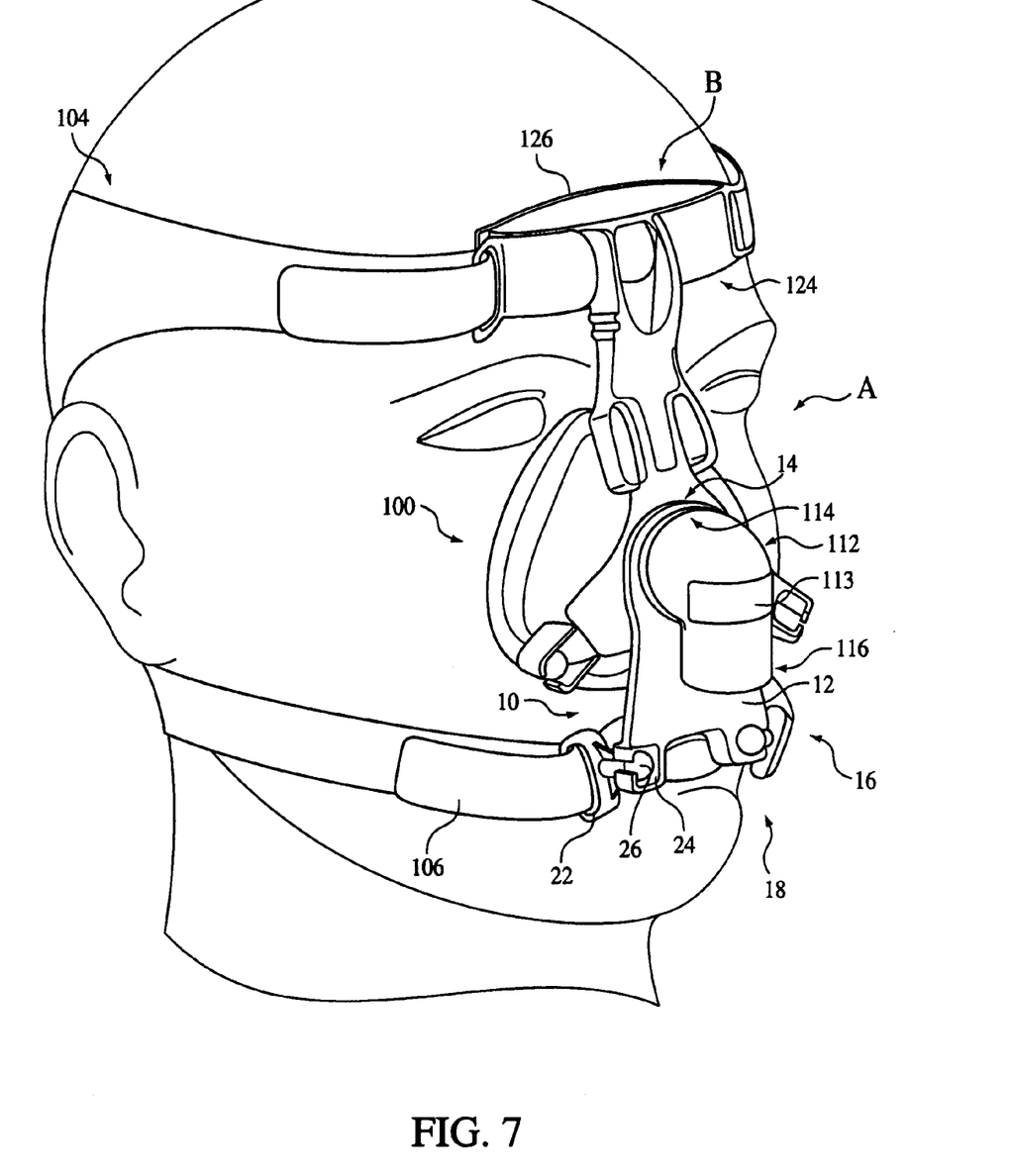
FIG. 7 is a perspective view of a mask mounting mechanism in use by a patient using a patient interface device and a mask attachment assembly.

Clip element 20 includes a catch 26 to engage slot 24. As shown in FIG. 3, the catch may have a ball-and-socket geometry to permit the clip to self-adjust relative to slot 24 which provides more comfort to the patient. The ball-and-socket configuration as shown and described in U.S. Pat. No. 7,066,179 ("the '179 patent") issued Jun. 27, 2006. The contents of the '179 patent is hereby incorporated herein by reference. Of course, catch 26 may have a variety of other configurations other than a ball-and-socket arrangement as shown and described in U.S. patent application Ser. No. 11/449,111 ("the '111 application") filed Jun. 8, 2006. The '111 application is hereby incorporated herein by reference. In this embodiment, catch 26 can be removably engaged within slot 24, and in another embodiment, catch 26 can be permanently connected within slot 24. Removable engagement would allow the patient to disconnect straps 106 from mask 102 in an easy movement, as opposed to the current requirement of disengaging straps 106 from a buckle 22, collar or other retention mechanism attached to mask 102. It is also envisioned that such a ball-and-socket arrangement or other similar strap attachment mechanisms can be used in conjunction with other portions of mask 102. As seen in FIG. 7, slots 24 could be positioned directly on mask 102 for use in attaching other straps 106 and other mask attachment assemblies 104.

Figure 8:
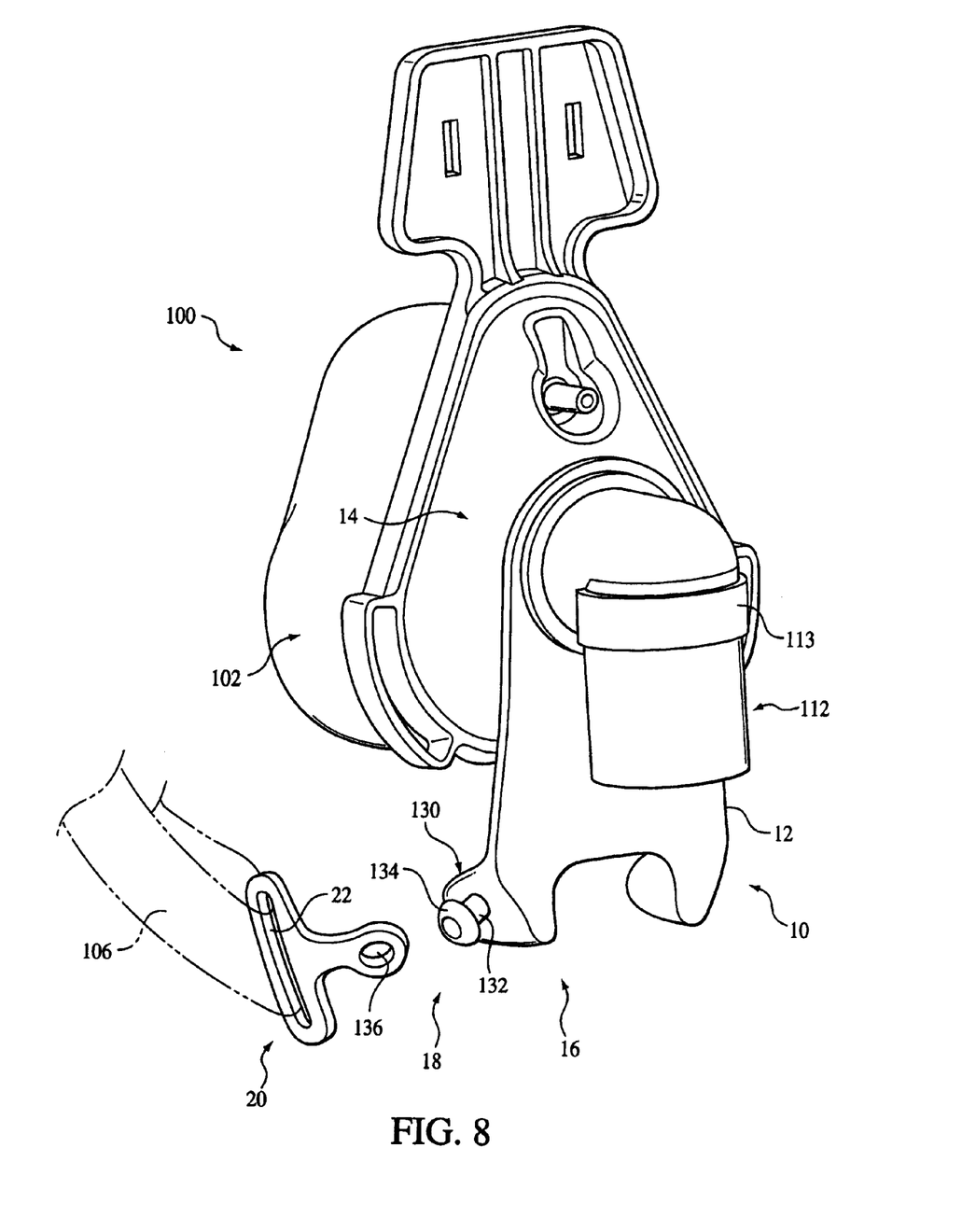
FIG. 8 is a perspective view of a further embodiment of a mask mounting mechanism according to the principles of the present invention as attached to a patient interface device.

Another embodiment of the present invention is illustrated in FIG. 8 utilizing an alternative attachment mechanism described and claimed in co-pending U.S. patent application Ser. No. 60/704,688, filed Aug. 2, 2005, which is also assigned to the Assignee of the present invention and incorporated herein by reference. In this embodiment, attachment mechanism 18 includes a button 130 extending from second end 16 of extension member 12. Button 130 includes a shaft 132 and a cap 134 having a diameter greater than the diameter of shaft 132. Accordingly, button 130 is substantially in the form of a mushroom. Of course, button 130 may have a variety of geometries without departing from the scope of the present invention. Further, attachment mechanism 18 also includes clip element 20. Clip element 20 includes an orifice 136 extending therethrough. Orifice 136 is sized and shaped so as to fit over cap 134 of button 130 and rest adjacent shaft 132.

In operation, orifice 136 of clip element 20 is removably attachable over cap 134 and is positioned adjacent shaft 132 between cap 134 and second end 16 of extension member 12. In addition, the diameter of orifice 136 is greater than the diameter of shaft 132, such that clip element 20 is rotatable around shaft 132. This provides additional rotating functionality to strap 106 associated with clip element 20.

Still further, clip element 20 of this embodiment is preferably formed from a substantially flexible material. This allows orifice 136 to be stretched and pushed over cap 134. However, once positioned over cap 134, orifice 136 reverts to its original shape and is therefore retained by cap 134. In addition, this flexibility allows the patient or user to easily remove and reattach clip element 20, which provides additional flexibility of movement and strap adjustment. Further discussion of the structure, operation, materials of construction and additional novel functionalities and benefits are set forth in the above-referenced patent application.

The present invention provides a mask mounting mechanism 10 and a patient interface device 100 that holds straps 106 of mask attachment assembly 104 spaced away from the user's face A. Any mask attachment assembly 104, such as a headgear apparatus, as is known in the art may be utilized with the present invention. Mask mounting mechanism 10 of the present invention increases the user's comfort by minimizing unnecessary contact with the user's face A. Mask mounting mechanism 10 also provides passive adjustability through the use of an adjustable attachment mechanism 18 and a pivotable extension member 12. Extension member 12 may also vary in length and orientation in order to modify the direction and amount of torque applied to mask 102 by straps 106. Moreover, due to the relative positioning of mask mounting mechanism 10, and extension member 12 in particular, even with the patient's movement and adjustment of strap 106, the seal between mask 102 and the user's face A remains intact. These features are particularly useful in a variety of applications, such as when the users are asleep. When asleep, it is common for many users to reorient their face resulting in differing forces being exerted on mask 102. The unique features of the present invention, as described above, are capable of self-adjustment to maximize comfort and maintain an adequate seal with the user's face A. Further, mask mounting mechanism 10 is capable of being retrofitted on a variety of presently-existing and prior art masks 102.

Although the invention has been described in detail for the purposes of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A mask mounting mechanism for use in connection with at least one strap of a patient interface device, the mask mounting mechanism comprising:

an extension member having a first end and a second end, the first end of the extension member attached to a portion of a mask, the second end of the extension member extending from and spatially separated from the mask; and an attachment mechanism positioned on the second end of the extension member and configured to engage the strap, wherein the extension member is configured to prevent the mask mounting mechanism or any portion of the patient interface device from contacting a user's chin when the mask and the mask mounting mechanism are donned by the user, wherein the extension member is further configured to be freely pivotable relative to the mask when the mask and the mask mounting mechanism are donned by the user, and wherein the second end of the extension member minimizes the potential for the attachment mechanism and the strap engaged therewith from contacting the user's face.

2. The mask mounting mechanism of claim 1, wherein the attachment mechanism comprises at least one clip element attached to a portion of the second end of the extension member, wherein the clip element includes a buckle for engaging the strap.

3. The mask mounting mechanism of claim 2, wherein the attachment mechanism further comprises at least one slot, and wherein a portion of the clip element is movingly engaged within the slot, such that the clip element and buckle are at least one of moveable and rotatable with respect to the second end of the extension member.

4. The mask mounting mechanism of claim 3, wherein the clip element includes a catch configured for engagement within the slot, which arrangement acts as a ball-and-socket arrangement.

5. The mask mounting mechanism of claim 4, wherein the catch is removably engaged or permanently connected within the slot.

6. The mask mounting mechanism of claim 3, wherein the clip element includes a clip element orifice configured to be removably attached over a button projecting from the second end of the extension member, the button having a shaft and a cap with a diameter greater than the shaft.

7. The mask mounting mechanism of claim 6, wherein the orifice includes a diameter greater than the diameter of the shaft, such that the clip element is rotatable around the shaft.

8. The mask mounting mechanism of claim 6, wherein the clip element is formed from a substantially flexible material, such that, in operation, the orifice can be stretched and pushed over the cap, and once positioned over the cap, the orifice reverts to its original shape and is therefore retained between the cap and the second end of the extension member.

9. The mask mounting mechanism of claim 1, wherein the first end of the extension member is attached to the mask at a position substantially adjacent a mask port extending through a mask wall, and the attachment between the extension member and the mask is permanent, integral, detachable, fixed, adjustable, moveable, rotatable or any combination thereof.

10. The mask mounting mechanism of claim 9, wherein the mask mounting mechanism further comprises a mask conduit connector configured to attach the first end of the extension member between an outer surface of the mask wall and a first end of a mask conduit coupling of a patient interface device that includes the mask.

11. The mask mounting mechanism of claim 10, wherein the mask conduit connector includes a rim portion and an extension portion, wherein the rim portion abuts a washer element, which abuts an inner surface of the mask wall, and wherein the extension portion extends through the mask port.

12. The mask mounting mechanism of claim 11, wherein the first end of the mask conduit coupling is engaged with the extension portion of the mask conduit connector.

13. The mask mounting mechanism of claim 10, wherein the first end of the mask conduit coupling includes a rim portion, wherein the rim portion abuts the first end of the extension member and urges the first end of the extension member against the outer surface of the mask wall.

14. The mask mounting mechanism of claim 1, wherein the extension member is manufactured from a substantially flexible material, a substantially rigid material, or a combination thereof.

15. A mask mounting mechanism for use in connection with a patient interface device having a mask, a mask attachment assembly having at least one strap and configured to retain the mask in a sealed position on a user's face, and a mask mounting mechanism, the mask mounting mechanism comprising:
- an extension means at least one of directly and indirectly attached to a portion of mask and extending from and spatially separated from the mask; and
- an attachment means positioned on the second end of the extension member for engaging the at least one strap of the mask attachment assembly,
- wherein the extension means is configured to prevent the mask mounting mechanism or any portion of the patient interface device from contacting a user's chin when the mask and the mask mounting mechanism are donned by the user, wherein the extension means is further configured to be freely pivotable relative to the mask when the mask and the mask mounting mechanism are donned by the user, and wherein the extension means minimizes the potential for the attachment means and at least a portion of the strap engaged therewith from contacting the user's face.

16. A patient interface device, comprising:
- a mask having a mask wall with a mask port extending therethrough;
- a mask conduit coupling in fluid communication with the mask port;
- a mask attachment assembly having at least one strap; and
- a mask mounting mechanism, including:
    - (i) an extension member having a first end and a second end, the second end of the extension member extending from and spatially separated from the mask; and
    - (ii) an attachment mechanism positioned proximate the second end of the extension member and configured to engage at least one strap of the mask attachment assembly, wherein the extension member is configured to prevent the mask mounting mechanism or any portion of the patient interface device from contacting a user's chin when the mask and the mask mounting mechanism are donned by the user, wherein the extension member is further configured to be freely pivotable relative to the mask when the mask and the mask mounting mechanism are donned by the user, and wherein the second end of the extension member minimizes the potential for the attachment mechanism and at least a portion of the strap engaged therewith from contacting the user's face.

17. The patient interface device of claim 16, wherein the mask attachment assembly is at least a three-point attachment assembly, wherein at least one of the attachment points is at the attachment mechanism of the mask mounting mechanism.

18. The patient interface device of claim 16, further comprising a forehead contact member attached to and extending from the mask, wherein at least a portion of the forehead contact member is configured to contact at least a portion of a user's forehead.

19. The patient interface device of claim 18, wherein the forehead contact member further includes a padded element for comfortably contacting the user's forehead.

20. The patient interface device of claim 16, wherein the mask conduit coupling has a first end and a second end, wherein the first end of the mask conduit coupling is attached to the mask, and the second end of the mask conduit coupling is in fluid communication with a patient circuit, a conduit, a pressure support device, a gas source, or any combination thereof.

* * * * *